United States Patent
Strömmer et al.

(10) Patent No.: US 7,590,217 B2
(45) Date of Patent: Sep. 15, 2009

(54) DIGITAL IMAGING METHOD AND APPARATUS FOR MAMMOGRAPHY

(75) Inventors: Pekka Strömmer, Espoo (FI); Timo Sulin-Saaristo, Helsinki (FI); Arto Virta, Helsinki (FI)

(73) Assignee: Planmed Oy, Helsinki (FI)

( * ) Notice: Subject to any disclaimer, the term of this patent is extended or adjusted under 35 U.S.C. 154(b) by 0 days.

(21) Appl. No.: 10/537,334

(22) PCT Filed: Dec. 4, 2003

(86) PCT No.: PCT/FI03/00930

§ 371 (c)(1), (2), (4) Date: Jun. 2, 2005

(87) PCT Pub. No.: WO2004/049946

PCT Pub. Date: Jun. 17, 2004

(65) Prior Publication Data

US 2006/0050843 A1 Mar. 9, 2006

(30) Foreign Application Priority Data

Dec. 4, 2002 (FI) .................................. 20022148

(51) Int. Cl.
*A61B 6/04* (2006.01)
*G21K 5/10* (2006.01)
*H01J 31/49* (2006.01)

(52) U.S. Cl. .......................... 378/37; 378/146; 378/189
(58) Field of Classification Search ............. 378/21–26, 378/37, 146, 93, 98.6, 119, 121–137, 145, 378/189

See application file for complete search history.

(56) References Cited

U.S. PATENT DOCUMENTS

| 4,203,037 | A | * | 5/1980 | Gur et al. ..................... 378/37 |
| 4,398,302 | A | * | 8/1983 | Pfeiler ........................ 378/146 |
| 4,628,356 | A | * | 12/1986 | Spillman et al. ........... 378/98.8 |
| 4,928,297 | A | * | 5/1990 | Tsutsui et al. ............... 378/146 |
| 5,164,976 | A | * | 11/1992 | Scheid et al. ............... 378/146 |
| 5,481,586 | A | | 1/1996 | Coe ........................... 378/146 |
| 5,526,394 | A | | 6/1996 | Siczek et al. ................. 378/37 |

(Continued)

FOREIGN PATENT DOCUMENTS

EP 1062913 12/2000

(Continued)

*Primary Examiner*—Edward J Glick
*Assistant Examiner*—Anastasia Midkiff
(74) *Attorney, Agent, or Firm*—Cozen O'Connor

(57) ABSTRACT

A digital imaging apparatus and method which includes a radiation source and a sensor arrangement for detecting radiation. The sensor arrangement contains one or more sensors formed of one or more preferably elongated sensor modules, which sensor module contains one or more pixel columns which receive image data. The digital imaging apparatus includes means for positioning the object to be Imaged which is situated within the area between the radiation source and the sensor arrangement, and means for limiting the beam from the radiation source essentially according to the active sensor surface of the said sensor arrangement. Also included is means to move the beam across the object being positioned to be imaged and means to move the at least one sensor belonging to the sensor arrangement in synch with the scanning movement of the beam in order to keep the active sensor surface essentially at right angles to the beam on the plane formed by the scanning movement.

30 Claims, 4 Drawing Sheets

U.S. PATENT DOCUMENTS

| | | | |
|---|---|---|---|
| 5,712,890 A * | 1/1998 | Spivey et al. | 378/37 |
| 5,872,364 A * | 2/1999 | Strommer | 250/370.09 |
| 6,164,820 A * | 12/2000 | Hell et al. | 378/193 |
| 6,292,531 B1 * | 9/2001 | Hsieh | 378/37 |
| 2003/0174806 A1 * | 9/2003 | Francke et al. | 378/37 |
| 2003/0194050 A1 * | 10/2003 | Eberhard et al. | 378/37 |
| 2004/0151277 A1 * | 8/2004 | Ohara | 378/37 |

FOREIGN PATENT DOCUMENTS

| WO | 0100092 | 1/2001 |
|---|---|---|

* cited by examiner

DIGITAL IMAGING METHOD AND APPARATUS FOR MAMMOGRAPHY

BACKGROUND OF THE INVENTION

The present invention relates generally to imaging of an object by electromagnetic radiation, especially to digital mammography.

1. Field of the Invention

More precisely, the invention relates to a digital imaging method in which the radiation that has passed through the object to be imaged is detected on at least one sensor, which contains one or more preferably elongated sensor modules, wherein the said sensor module contains one or more pixel columns which receive image data, in which method the object to be imaged is arranged essentially motionless and is scanned across with a beam which originates from a radiation source, the focus of which being essentially motionless in space, the beam being limited to be narrower than the object to be imaged and adapted essentially to the active surface of the sensor, and in which method the sensor is moved in synch with the scanning movement of the beam while at the same time the said active surface is kept essentially at right angles to the beam on the plane formed by the scanning movement of the beam.

The invention also relates to a digital imaging apparatus, which includes a radiation source, a sensor arrangement for detecting radiation, which arrangement contains one or more sensors formed of one or more preferably elongated sensor modules, which sensor module contains one or more pixel columns which receive image data, means for positioning the object to be imaged, the said means being situated within the area between the radiation source and the sensor arrangement, means for limiting the beam from the radiation source essentially according to the active sensor surface of the said sensor arrangement, means to move the beam across the object being positioned to be imaged and means to move the said at least one sensor belonging to the sensor arrangement in synch with the said scanning movement of the beam and to keep the said active sensor surface essentially at right angles to the beam on the plane formed by the scanning movement.

2. Description of Prior Art

In medical x-ray technique digital imaging provides certain advantages compared to the use of film. For example, fewer retakes are needed when a separate photograph developing stage is left out and when a major portion of the "failed" images even may be programmatically adjusted into a form still diagnostically applicable. On the other hand, the radiation dose the patient is exposed to decreases due to the semiconductor sensors being more sensitive than analogous films. While health care and hospital systems move more and more to digital technique in general and thus also to handling the x-ray images and patient information etc. in digital form, there additionally arises new possibilities and advantages related, among other things, to viewing, handling, storing and remote observing of the images having been taken and stored in digital form.

Semiconductor sensors for digital imaging purposes are typically radiation sensitive surfaces formed of small picture elements, or pixels, the extreme case of such surfaces being a line detector with a single line. The electromagnetic radiation, such as light, infra-red or x-ray radiation, which has been absorbed to the area of the pixels forms an electric charge corresponding the quantity and energy of the radiation quanta. So, when the electric charge is formed as a function of time, i.e. when during the 'exposure time' a pixel integrates the electric charge formed within its area, the level of the pixel signal may be adjusted in principle by altering the integration time. However, varying of the integration time does not affect sensitivity of the sensor.

Digital imaging may be implemented as full field imaging where a sensor according to (at least) the dimensions of the object is used, or as scanning imaging where a narrow sensor is used. In view of a practical imaging process, full field imaging corresponds to the traditional imaging onto a film of the size of the whole imaging area. A clear disadvantage of this technology is the need for sensors that are large in area and thus very expensive, and on the other hand the need to take into account the secondary radiation scattering from the object being imaged, which requires e.g. arranging complex mechanical grid structures in front of the detector. Because of their operational principle, the grid structures also even double the radiation dose needed for the imaging.

Narrow sensor is typically used in scanning technique, which requires some mechanics for support. However, such a solution is considerably more economical in total costs than solutions based on a full field sensor, especially due to its smaller sensor area. In scanning imaging also the grid structure may be left out.

Due to the high resolution, i.e. small pixel size needed in mammography, scanning imaging requires in practise use of a sensor of several pixels wide and a so called TDI method (Time Delay Integration) in order to achieve a signal that would be adequate for detecting the radiation by radiation-production of a practical magnitude. Although there are some other possibilities, TDI imaging is usually implemented by CCD sensor technique (Charge Coupled Device).

In U.S. Pat. No. 5,526,394 there has been presented a prior art digital scanning imaging solution, according to which scanning movement of the beam and the corresponding movement of the sensor arrangement is implemented in a mammography apparatus in mechanical connection with each other with the help of a pendulum in such a way that a collimation element limiting the beam and the sensor arrangement move along a concentric curved path. In the apparatus in question also the compression paddles, which position the tissue to be imaged, have been arranged curved according to the trajectory of the sensor arrangement. The focus of the swinging movement in the apparatus has been arranged to be situated on the level of the focus of the radiation source.

Although it is in principle mechanically simple to keep the sensor arrangement at right angles to the beam according to the solution of the above-mentioned publication, use of it also causes certain problems. For example, as it has been customary in mammography to position and compress the object to be imaged motionless between plane-like compression paddles, the curved compression surfaces are difficult to approve for many people to begin with. Practical problems may also occur, especially when small breasts are being positioned between wide curved surfaces. Additionally, such a way of positioning the object causes the imaging geometry becoming different compared to the traditional one, which geometry is further affected differently by the thickness of the tissue to be imaged than in the traditional solution. Furthermore, when using curved surfaces, typical special imaging modes used in mammography, such as enlargement, spot and stereotaxic imaging must be implemented in a completely new way, in which case they require specific solutions of their own, and all the traditional imaging modes are not even realizable in connection with such a solution—at least not without completely new special arrangements.

One of the main objects of the present invention is to promote development in digital mammography in such a way that even when scanning imaging is used, from the user's point of view both imaging apparatus and the image to be formed essentially correspond to the traditional film-based full field imaging, i.e. that in case so desired, the invention may be implemented "in a way which is (in principle) invisible to the user of the mammography apparatus". Thus, an additional object of the invention is to enable modifying the existing film-based devices to digital ones with as small changes and costs as possible.

The essential features of the invention are expressed more precisely in the attached claims. These features include that when during the imaging scan the sensor surface is kept continuously at right angles to the beam on a plane formed by its scanning movement, alike according to prior art, the sensor is not moved along a curved path in direction of the scanning movement but essentially along a linear path.

BRIEF DESCRIPTION OF THE DRAWINGS

In the following the invention is described more closely with the help of its preferable embodiments and by referring to the following figures, of which figures.

DETAILED DESCRIPTION OF THE INVENTION

Figure 1:
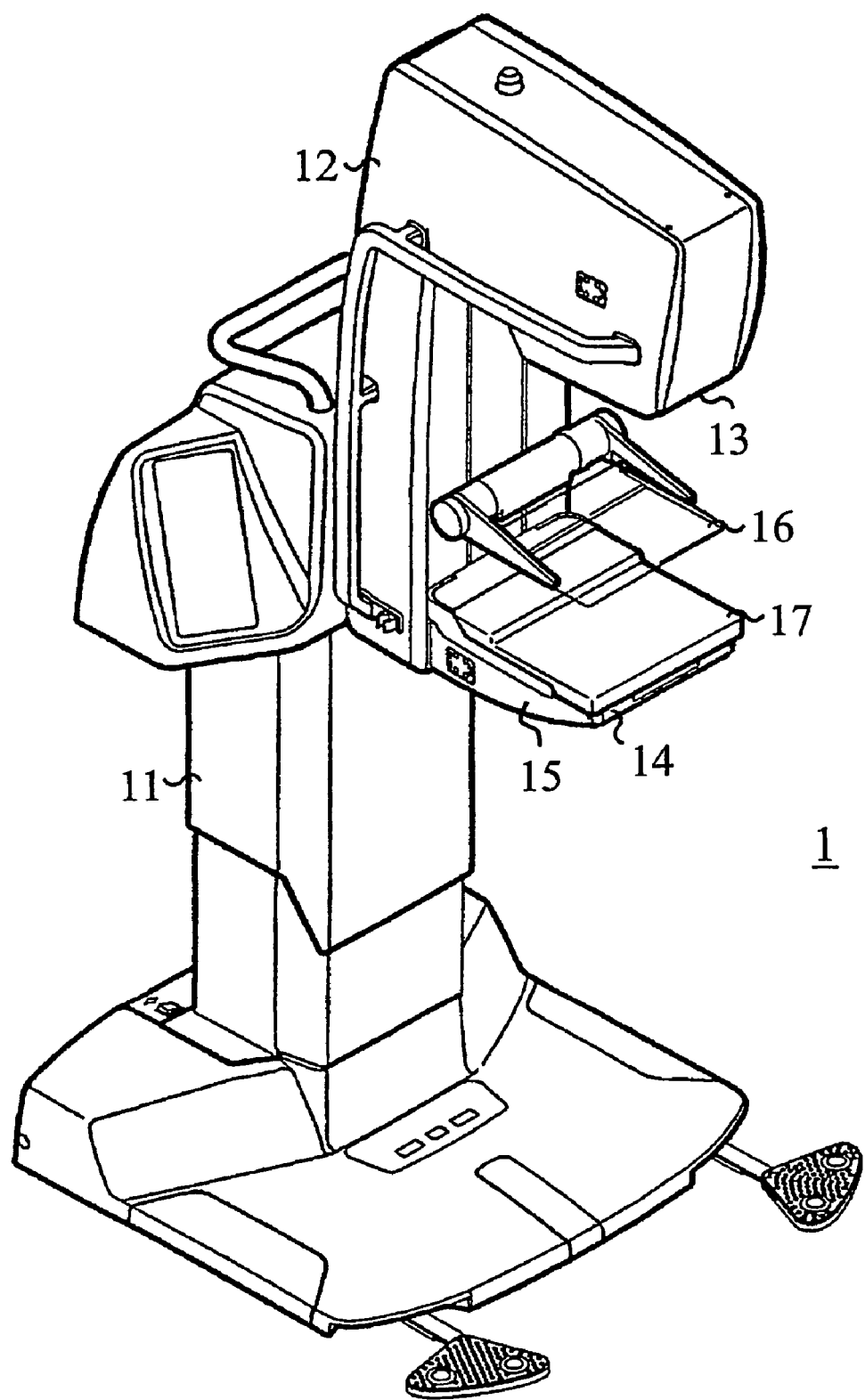
FIG. 1 presents a typical mammography apparatus.

The mammography apparatus 1 presented in FIG. 1 consists of a body part 11 and a C-arm 12 connected to it. Typically a radiation source 13 and, e.g. inside the lower shelf 14, image data receiving means 15 are placed on the opposite ends of the C-arm 12, which imaging means 13, 15 when being situated inside the cover of the apparatus are not actually visible in FIG. 1. Additionally, means 16, 17 for positioning the object to be imaged within the imaging area are located within the area between these imaging means 13, 15, typically near the image data receiving means 15. Typically, the C-arm 12 is movable both in vertical direction in relation to means 16, 17 for positioning the object to be imaged and rotatable in relation to the body part 11. The positioning means 16, 17 are typically formed of an upper compression paddle 16 and a lower compression paddle 17, which lower compression paddle 17 may be arranged to function as a so called bucky as well. Bucky means a grid structure located between the tissue to be imaged and the image data receiving means, which grid structure restricts access of the radiation scattered from the tissue to the image data receiving means.

Figure 2:
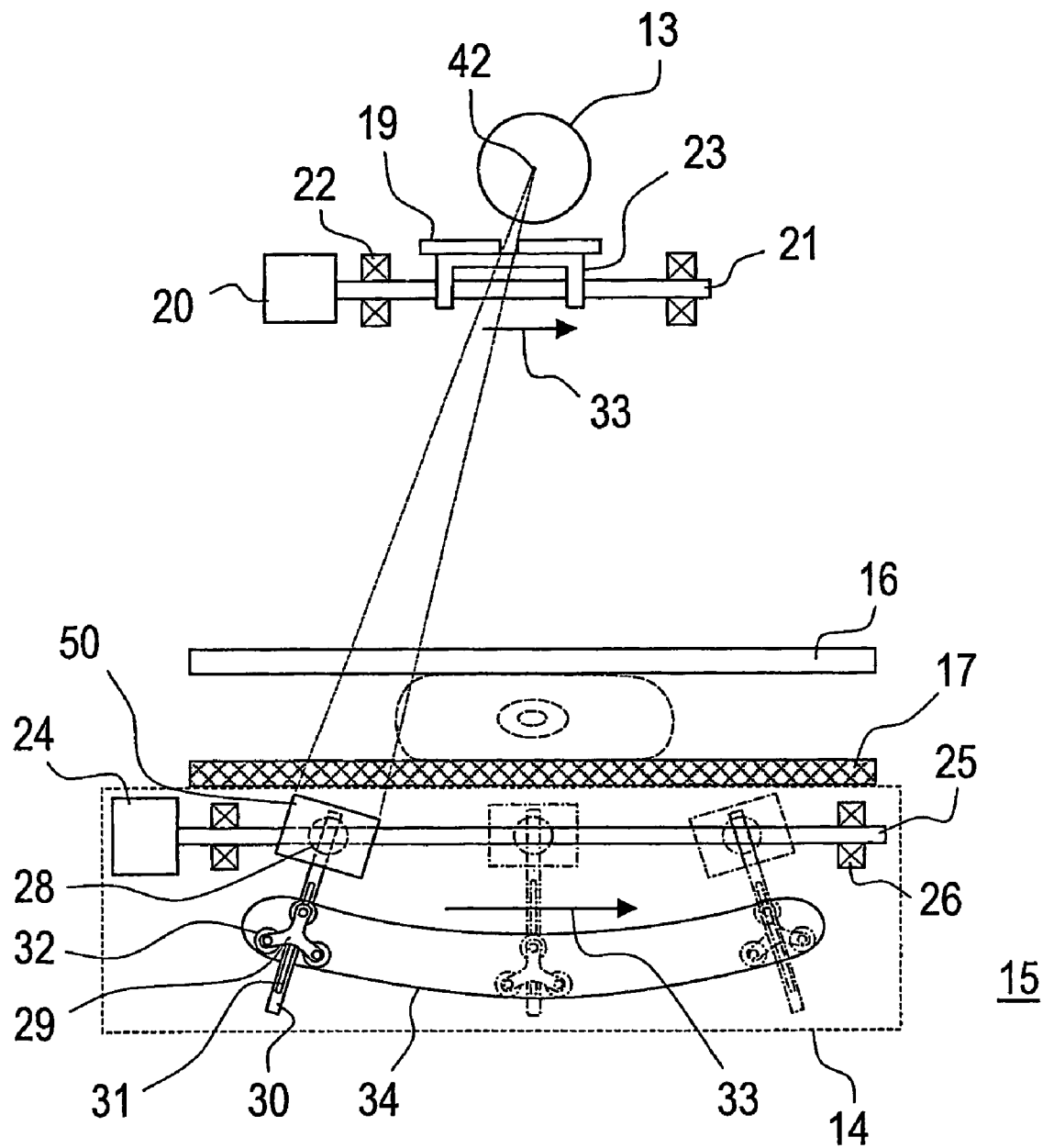
FIG. 2 presents one way of implementing a linear scanning movement of the sensor according to the invention.

In FIG. 2, which is not drawn in scale, is presented in a simplified manner one way to implement a sensor arrangement 15 of a mammography apparatus according to the invention. In the upper part of FIG. 2 there is presented a radiation source 13 and its focus 42, the radiation source being situated at the first end of the C-arm 12. Between the radiation source 13 and the object to be imaged there is a collimator apparatus including a collimator 19, which is arranged to be moved in synch with at least one sensor 50 belonging to the sensor arrangement 15 of the imaging apparatus. The collimator apparatus consists of an actuator 20, such as a motor, which may be operated programmatically and makes a bearing-mounted 22 screw 21 rotate. In the collimator 19 there are ledges 23 or equivalent, which include such an inner thread fitted to the screw 21 that when the screw 21 is rotated, the collimator 19 moves in direction of the middle axis of the screw 21. In FIG. 2 the arrow 33 presents the direction of the scanning movement of the beam defined by the collimator 19.

In the solution according to FIG. 2, the radiolucent upper and lower compression paddles 16, 17 function as positioning means of the object to be imaged, which compression paddles are located between the radiation source 13 and the lower shelf 14, which is situated at the other end of the C-arm in such a way that the lower shelf 14 is situated near the lower surface of the lower compression paddle 17. The lower shelf 14 as such can be arranged to function also as the lower compression paddle 17. The surfaces of the compression paddles 16, 17, which become against the object to be imaged, are essentially plane-like.

The sensor arrangement 15, which is situated in the essential vicinity of the lower compression paddle 17 inside the lower shelf 14, is implemented according to FIG. 2 by connecting the image data receiving sensor 50 to a transmission element 28, which is equipped with an inner thread and through which extends a rotatable bearing-mounted 26 screw 25, said screw being preferably programmatically operable by an actuator 24, such as a motor. When the screw 25 rotates, the sensor 50 moves in a linear fashion in the direction of the middle axis of the screw 25. Additionally, a bearing-mounted or an articulated connection has been arranged between the transmission element 28 and the sensor 50 to enable their mutual rotational movement. Further, a longitudinal control arm 30 is attached motionless to the sensor 50, which control arm is essentially straight and extends away from the sensor 50 in direction of the beam. Further, in the control arm 30 there is a longitudinal trajectory groove 31 extending essentially in the direction of the beam, in which groove there is fitted a control element 29, respectively, which can thus move in the direction of the longitudinal axis of the control arm 30. The control element 29 according to FIG. 2 consists of a body, which has three projections extending outwards from the centre of the body, the projections being at 120° angles to each other and having rollers 32 at their ends. The rollers 32 are pivoted to be rotatable around their middle axles. Within the lower shelf 14 there is further arranged a longitudinal curved guide groove 34, the radius of curvature of which corresponds the distance of the groove 34 from the focus 42 of the radiation source 13. The control element 29 is arranged movable in the guide groove 34.

In practise, the solution according to FIG. 2 functions such that when the sensor 50 is moved essentially linearly along the screw 25 by control of the actuator 24, whereby it concurrently moves the control element 29 along the curved guide groove 34, position of the sensor 50 in relation to the direction of the linear movement determined by the screw 21 continuously tilts in such a way that the active surface of the sensor 50 remains essentially at right angles to the beam on the plane formed by the scanning movement of the beam, because of being guided by the shape of the guide groove 34 as well as the structures arranged for the control arm 31 and the transmission element 28. During the imaging scan the control arrangement of the imaging apparatus 1 controls the actuators 20, 24 which rotate the screws 21 and 25 in such a way that during the imaging scan the beam originating from the radiation source 13 and being defined by the collimator 19 moves in synch with the active surface of the sensor 50, i.e. in a way that the collimator 19 and the sensor 50 move in the same direction with speeds synchronized with each other.

The linear movement of the collimator 19 and the sensor 50 can be arranged synchronized also by connecting them together mechanically. Likewise, means may be arranged to the collimator 19 for adjusting the width of the beam during the imaging scan.

Figure 3:
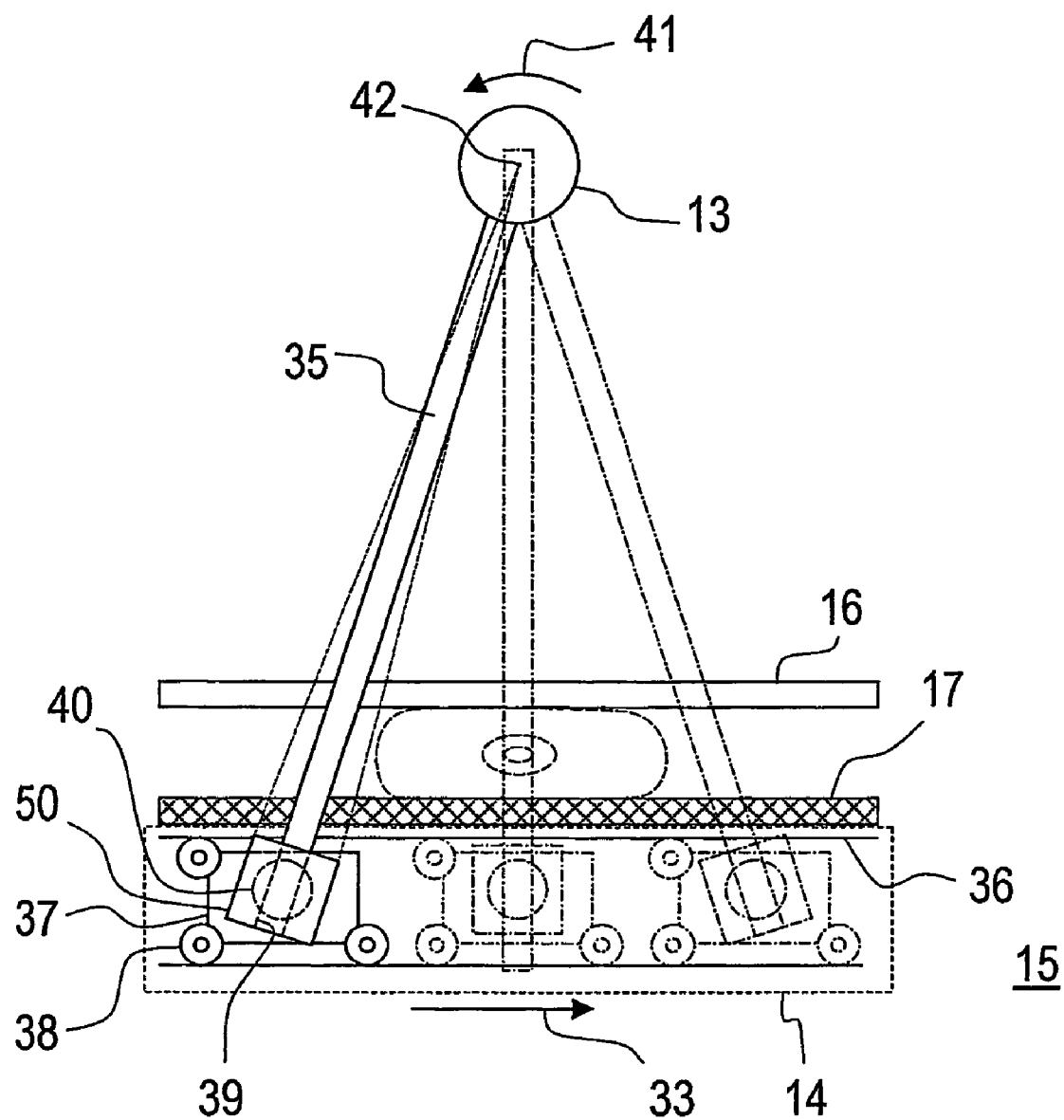
FIG. 3 presents another possible way of implementing a linear scanning movement of the sensor according to the invention and FIGS. 4 and 5 present one sensor module structure well-suited to be used in mammography.

In FIG. 3, which is not drawn in scale either, is presented in a simplified manner another way of implementing the sensor arrangement 15 of the mammography apparatus 1 according to the invention. In this solution, a pendulum arm 35 is arranged to the imaging apparatus, the focus of rotation of which being arranged on the level of the focus 42 of the radiation source 13. Moving of the collimator 19 (not shown in FIG. 3), which is arranged in close proximity to the radiation source 13, may be implemented not only as according to FIG. 2 but also by arranging it in mechanical connection with the pendulum arm 35 in such a way that the collimator 19 follows the movements of the pendulum arm 35. Such a structure additionally includes an actuator (not shown in the figure) for producing the movement 41 of the pendulum arm 35 with respect to the focus of rotation 42.

In the solution according to FIG. 3, the sensor 50 receiving image information is attached motionless to the lower part of the pendulum arm 35 with the exception that it is allowed to move in the direction of the longitudinal axis of the pendulum arm 35, e.g. along a guide groove 39 arranged to the pendulum arm 35. Additionally, a transmission element 40 is connected to the sensor 50, which element is connected by a bearing-mounted or an articulated connection to a control element 37 equipped with wheels 38 to enable mutual rotational movement between the sensor 50 and the control element 37. This makes possible moving the sensor 50 along a linear guide groove 36 arranged inside the lower shelf 14 with the help of the pendulum arm 35 in such a way that because of the control provided by the structures arranged for the transmission element 40 and the control element 37, i.e. when moving in relation to the pendulum arm 35 only in the direction of the beam, the sensor remains continuously essentially at right angles to the beam on a plane formed by its scanning movement. If movement of the radiation source 13, and/or that of the collimator 19 being arranged in close proximity to it, is mechanically connected to the movement of the pendulum arm 35, too, the scanning movement of the beam and the sensor 50 can be synchronized by a mechanically forced control.

The solution according to FIG. 3 can be modified e.g. such that the sensor 50 is attached to the pendulum arm 35 completely motionless and the pendulum arm 35 will be provided with means, such as a telescope structure, for altering its length in such a way that the movement of the sensor 50 in the scanning direction becomes linear. This makes it possible to implement the lower shelf 14 of the imaging apparatus 1 in a manner which is relatively simple and even less bulky.

It is self-evident to a person skilled in the art that moving of the sensor can be implemented by other means than those presented above, too, e.g. by arranging a separate actuator to tilt the sensor or by moving the sensor and/or a guide element attached motionlessly to it in a guide groove or a tunnel, which is designed such that also the sensor movement according to the invention will be accomplished by a mechanically forced control. Likewise, the possible linear movement of the collimator may be implemented by a corresponding manner self-evident to a person skilled in the art as the linear movement of the sensor. More generally speaking, when considering the structure of an existing film based mammography apparatuses, perhaps solutions most corresponding to their outer dimensions and where minimum changes are required can be reached by arranging both the linear and tilting movement of the sensor to be implemented with separate actuators.

Naturally, separate actuators may also be arranged for realizing all the movements needed for accomplishing the scanning movement of the beam.

Figures 4, 5:
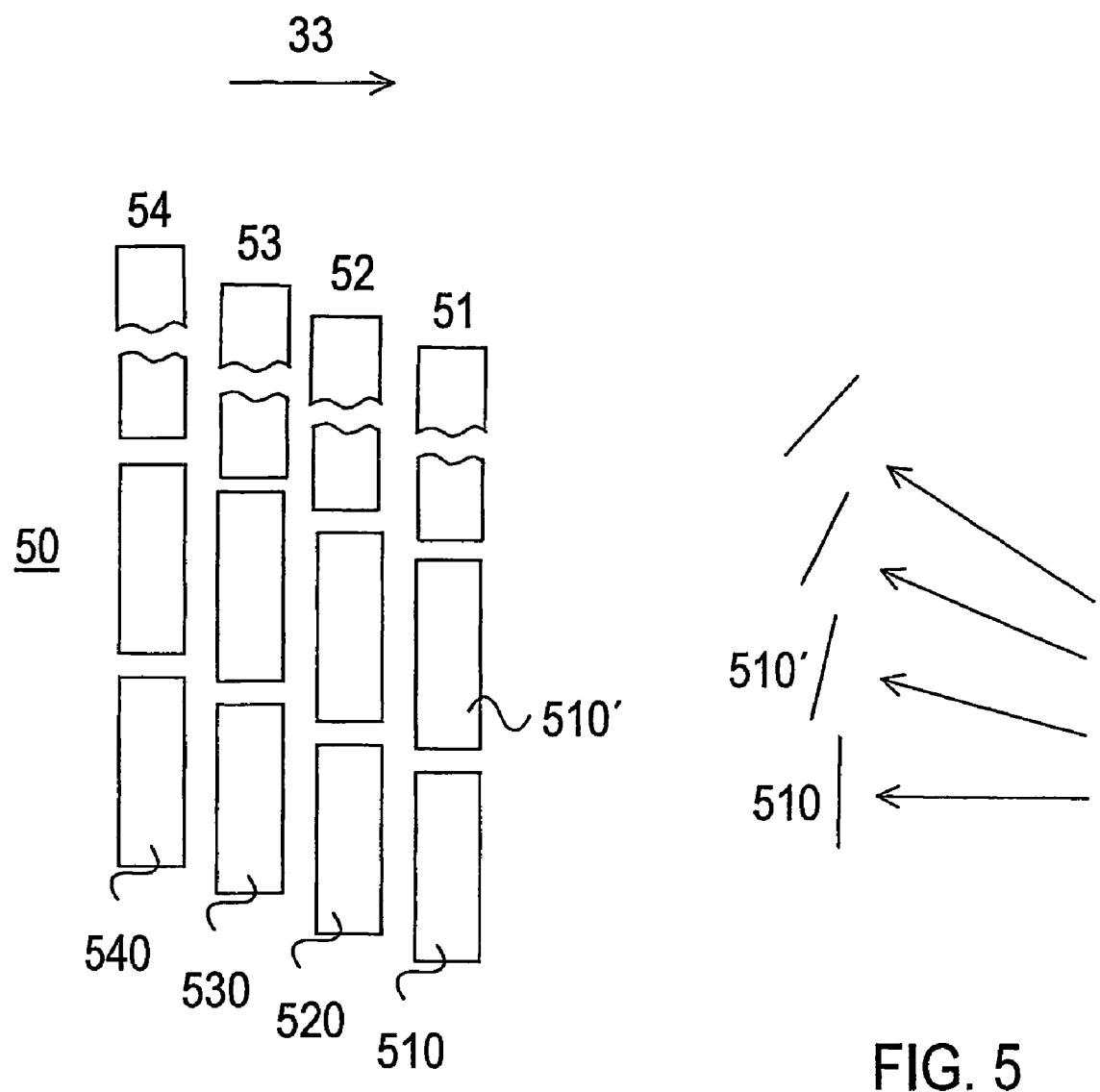

In FIG. 4 there is presented one practical sensor module solution to form a TDI sensor suitable for use in scanning imaging. The sensor 50 can consist of e.g. four in the scanning direction consecutive sensor module columns 51, 52, 53, 54, in which columns separate sensor modules 510-540, 510' are placed at right angles to the scanning movement 33 in slightly different positions such that the possible seams of the sensor surfaces of the modules 510-540, 510' will become placed at slightly various heights in each column. This secures that the possible gaps between the modules 510-540, 510' will be imaged anyhow via the three other module columns and no gaps will be left in the image formed. The overlap may be implemented by e.g. as a multiple of the pixel size of the sensor module added with a quotient, which depends on the number of modules involved in the image formation and the pixel size according to a calculation formula dpix x (n+1/m), where dpix= diameter of the pixel, n=integer and m=number of the modules in the observation direction or an integer smaller than that, whereby the imaging resolution of the sensor module may be increased to be higher than that of the physical pixel size with the help of signal processing functions.

The corresponding overlaps and distances between the modules 510-540, 510' may also be implemented between those sensor modules consecutive in the scanning direction, whereupon also the resolution in the direction of the scanning movement may be increased correspondingly. On the other hand, separate sensor modules 510-540 510' may be clocked in a way self-evident to a person skilled in the art to achieve a corresponding effect that increases resolution also in the direction of the scanning movement.

In mammography applications a single module 510-540, 510' may be formed of e.g. 142×284 pixels of 35 mm and may form a sensor surface of an area of 10 mm×10 mm, when the sensor arrangement as a whole may contain e.g. in the width direction four and in the height direction about 20 such modules, thereby forming a sensor 50 of ca. 20 mm by width and e.g. ca. 240 mm by heidth.

It is recommended to keep the gaps between the sensor modules 510-540, 510' as small as possible not only in view of the physical dimensions of the sensor arrangement 15 as a whole but also in order to keep the imaging time needed for implementing the scanning movement as short as possible, so that unnecessary problems would not be created due to a possible uneven production of radiation in the radiation source or as a consequence of the object to be imaged moving during the imaging scan. In view of forming a seamless image the distance between the modules 510-540, 510' is not critical. For example, a shift register may be arranged on the other of the vertical edges of each sensor module 510-540, 510' without the space occupied by it essentially troubling the imaging.

In FIG. 5 it has been clarified how in the module column formed of two or more sensor modules 510-540, 510' each of the modules may be placed essentially at right angles to the focus 42 of the beam used in the imaging also in the direction perpendicular to the scanning direction.

The invention is described above only with the help of a few possible embodiments. It is self-evident to a man skilled in the art that the basic idea of the invention may be implemented in several different ways and its various embodiments are not limited to the examples described above but they may vary within the scope of protection defined in the following patent claims.

The invention claimed is:

1. A digital mammography imaging method comprising the steps of:
    using at least one sensor to detect radiation passed through an object, each of the at least one sensor containing at least one sensor module, wherein the at least one sensor module contains one or more pixel columns which receive image data,
    arranging the object to be imaged in a compression structure that is essentially motionless, the compression structure comprising an essentially plane-like upper compression paddle and an essentially plane-like lower compression paddle or a shelf having an essentially plane-like top surface,
    scanning continuously across said object with a beam which originates from a radiation source having a focus, the focus of the radiation source being essentially motionless in space, the beam being limited to be narrower than the object to be imaged and adapted essentially to an active surface of the at least one sensor, and
    moving the at least one sensor in synch with the scanning movement of the beam while at the same time the active surface is kept essentially at right angles to the beam on a plane formed by the scanning movement of the beam, wherein movement of the at least one sensor is implemented by continuously adjusting the distance of the at least one sensor from the radiation source in such a way that the trajectory of the at least one sensor in the direction of the scanning movement of the beam becomes essentially linear, wherein said essentially linear movement of the at least one sensor takes place beneath the lower compression paddle or top surface of the shelf.

2. The imaging method according to claim 1, wherein the movement of the at least one sensor is realized by one or more actuators.

3. The imaging method according to claim 1, wherein at least a part of the movements of the at least one sensor are realized by mechanically forced control.

4. The imaging method according to claim 1, wherein said at least one sensor is moved in a such a way that the sensor is connected to a transmission element, which is moved along an essentially linear trajectory and the said connection is realized in such a way that the connection enables mutual rotational movement of the transmission element and the at least one sensor in the direction of said linear movement, whereby the said condition of perpendicular orientation of the sensor surface is realized by tilting the at least one sensor with respect to the said transmission element.

5. The imaging method according to claim 1, wherein said at least one sensor is arranged in functional connection with a control element, said control element enables altering the distance between the at least one sensor and the control element in the direction of the beam, said control element is moved along a curved trajectory and the distance between said at least one sensor and the control element is modified during the scanning of the beam in such a way that the trajectory of the sensor becomes linear.

6. The imaging method according to claim 5, wherein said control element is moved in a guide groove, the curvature of radius of the guide groove corresponding to the distance between said control element and the focus of the radiation source.

7. The imaging method according to claim 4, wherein said transmission element or a control element is moved integrated with a pendulum arm, the centre of rotation of said arm being situated on the level of the focus of the radiation source.

8. The imaging method according to claim 1, wherein the scanning movement of the beam is realized by moving a collimation element that limits the beam with the help of an actuator.

9. The imaging method according to claim 1, wherein a collimation element that limits the beam is moved essentially in parallel with the said linear movement of the sensor.

10. The imaging method according to claim 1, wherein the scanning movement of the beam is realized by moving a collimation element which limits the beam along a curved path, the curvature of radius of which corresponding to the distance between the said collimator and the focus of the radiation source.

11. The imaging method according to claim 9, wherein the radiation source is swivelled and the scanning movement of the beam is realized by moving said collimation element in mechanical contact with the swiveling movement of the radiation source.

12. The imaging method according to claim 9, wherein the movement of the collimation element and the linear movement of the at least one sensor is synchronized mechanically.

13. The imaging method according to claim 12, wherein the movement of the collimation element and the at least one sensor in the direction of the scanning movement of the beam is synchronized by connecting the at least one sensor mechanically to a swiveling movement of the radiation source.

14. The imaging method according to claim 1, wherein the sensor or sensors are arranged to be formed, at right angles to the plane formed by the scanning movement, of at least one sensor column containing two or more modules and the active surface of each of the modules also being positioned at right angles with respect to the focus of the beam.

15. The imaging method according to claim 1, wherein the compression structure comprises one or two compression paddles, one or both of which are radiolucent.

16. A digital mammography imaging apparatus, comprising:
    a radiation source having a focus, the focus of the radiation source being essentially motionless in space,
    a sensor arrangement for detecting radiation, which arrangement contains at least one sensor formed of at least one sensor module, the at least one sensor module containing one or more pixel columns which receive image data,
    a compression structure for positioning an object to be imaged, located within an area between the radiation source and the sensor arrangement, the compression structure comprising an essentially plane-like upper compression paddle and an essentially plane-like lower compression paddle or a shelf having an essentially plane-like top surface,
    means for limiting a beam from the radiation source essentially according to an active sensor surface of the said sensor arrangement,
    means for scanning continuously across said object with a beam which originates from the radiation source, and
    means for moving the said at least one sensor which belongs to the sensor arrangement in synch with the scanning movement of the said beam and keeping the said active sensor surface essentially at right angles to the beam on a plane formed by the scanning movement,
    wherein the imaging apparatus includes means for continuously adjusting the distance of the at least one sensor from the radiation source in such a way that the trajectory of the at least one sensor in the direction of the scanning movement of the beam becomes essentially linear and takes place beneath the lower compression paddle or beneath top surface of the shelf.

17. The imaging apparatus according to claim 16, wherein the apparatus includes at least one actuator for implementing the movement of the at least one sensor.

18. The imaging apparatus according to claim 16, wherein the apparatus includes means for implementing at least a part of the movements of the at least one sensor by mechanically forced control.

19. The imaging apparatus according to claim 16, wherein the apparatus includes means for linearly moving the at least one sensor and means for tilting the at least one sensor by a mechanically forced control along with the linear movement.

20. The imaging apparatus according to claim 16, wherein the apparatus includes a transmission element arranged to be connected to the at least one sensor and means for linearly moving the transmission element and for tilting the at least one sensor in relation to the transmission element in the direction of the said linear movement.

21. The imaging apparatus according to claim 16, wherein the apparatus includes a control element arranged to be moved along a curved trajectory in the direction of the scanning movement of the beam, which control element is arranged in a functional connection with said at least one sensor in such a way that their mutual distance in the direction of the beam is adjustable.

22. The imaging apparatus according to claim 21, wherein in order to form said curved trajectory, the apparatus includes a guide groove, the radius of curvature of said groove corresponding to the distance between the groove and the focus of the radiation source.

23. The imaging apparatus according to claim 22, wherein the apparatus includes a pendulum arm, the center of rotation of said arm being arranged on the level of the focus of the radiation source, whereby either a transmission element arranged to the apparatus or said control element, or both of them, is attached to the pendulum arm in such a way that the sensor or sensors can move in the direction of the longitudinal axis of the pendulum arm, or the pendulum arm itself has been arranged to be adjusted by its length.

24. The imaging apparatus according to claim 16, wherein the imaging apparatus includes means for moving a collimator element that limits the beam essentially in parallel with the linear movement of the sensor.

25. The imaging apparatus according to claim 16, wherein the apparatus includes means for moving a collimator element that limits the beam along a curved path, the radius of curvature of which corresponds to the distance between the collimator element and the focus of the radiation source.

26. The imaging apparatus according to claim 18, wherein at least one of means for moving the beam and the at least one sensor is arranged in mechanical contact with a pendulum arm, the center of rotation of said arm being arranged on the level of a focus of the radiation source.

27. The imaging apparatus according to claim 26, wherein the collimator element, the at least one sensor and the radiation source are arranged in mechanical contact with the said pendulum arm in such a way that the said synchronization of the scanning movement of the beam and the movement of the at least one sensor takes place in a forced manner while the said pendulum arm is moved by an actuator.

28. The imaging apparatus according to claim 17, wherein the apparatus includes actuators for realizing all the movements of the at least one sensor and the means for limiting the beam.

29. The imaging apparatus according to claim 16, wherein the at least one sensor is arranged to be formed, in the direction at right angles to the plane formed by the scanning movement, of at least one sensor column which contains two or more modules, and the active surface of each module also being positioned also at right angles to the focus of the beam.

30. The imaging apparatus according to claim 16, wherein the radiation source is stationary in space but arranged to be rotated about itself.

* * * * *